(12) United States Patent
Ujita et al.

(10) Patent No.: US 9,227,911 B2
(45) Date of Patent: Jan. 5, 2016

(54) METHOD FOR PRODUCING (R)-1, 1, 3-TRIMETHYL-4-AMINOINDANE

(71) Applicant: SUMITOMO CHEMICAL COMPANY, LIMITED, Tokyo (JP)

(72) Inventors: Satoru Ujita, Takarazuka (JP); Tsutomu Matsumoto, Osaka (JP); Tomohiko Inui, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/418,872

(22) PCT Filed: Aug. 28, 2013

(86) PCT No.: PCT/JP2013/073730
§ 371 (c)(1),
(2) Date: Jan. 30, 2015

(87) PCT Pub. No.: WO2014/034957
PCT Pub. Date: Mar. 6, 2014

(65) Prior Publication Data
US 2015/0203438 A1   Jul. 23, 2015

(30) Foreign Application Priority Data
Aug. 31, 2012 (JP) .................................. 2012-191526

(51) Int. Cl.
C07C 209/88 (2006.01)
C07C 51/41 (2006.01)
C07C 59/255 (2006.01)
C07C 211/60 (2006.01)
C07B 57/00 (2006.01)
C07C 57/00 (2006.01)

(52) U.S. Cl.
CPC ............... *C07C 209/88* (2013.01); *C07B 57/00* (2013.01); *C07C 51/412* (2013.01); *C07C 59/255* (2013.01); *C07C 211/60* (2013.01); *C07C 2102/08* (2013.01)

(58) Field of Classification Search
CPC .................................................... C07C 209/88
See application file for complete search history.

(56) References Cited

FOREIGN PATENT DOCUMENTS

| | | |
|---|---|---|
| JP | 4-54173 A | 2/1992 |
| JP | 4-108774 A | 4/1992 |
| JP | 2012-25735 A | 2/2012 |
| WO | WO 2011/162397 A1 | 12/2011 |

OTHER PUBLICATIONS

The International Preliminary Report on Patentability and an English translation of the Written Opinion of the International Searching Authority, dated Mar. 12, 2015, issued in the corresponding International Application No. PCT/JP2013/073730.
International Search Report, issued in PCT/JP2013/073730, dated Nov. 26, 2013.

*Primary Examiner* — Brian J Davis
(74) *Attorney, Agent, or Firm* — Birch, Stewart, Kolasch & Birch, LLP

(57) ABSTRACT

A method for producing a methanol solvate of D-tartrate of (R)-1,1,3-trimethyl-4-aminoindane, the method comprising steps (a), (b), and (c) below, and comprising adding water to a reaction system before step (c):
  step (a) of mixing 1,1,3-trimethyl-4-aminoindane, D-tartaric acid, and methanol to provide a mixture containing a methanol solvate of D-tartrate of (R)-1,1,3-trimethyl-4-aminoindane;
  step (b) of cooling the obtained mixture; and
  step (c) of retrieving the methanol solvate of D-tartrate of (R)-1,1,3-trimethyl-4-aminoindane.

13 Claims, No Drawings

METHOD FOR PRODUCING (R)-1,1,3-TRIMETHYL-4-AMINOINDANE

TECHNICAL FIELD

The present invention relates to a method for producing (R)-1,1,3-trimethyl-4-aminoindane and others.

BACKGROUND ART

Patent Document 1 describes that (R)-1,1,3-trimethyl-4-aminoindane represented by formula (1)

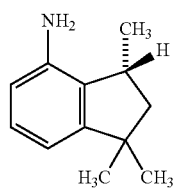
(1)

is a useful synthetic intermediate of an agricultural and horticultural fungicide having a plant disease-control effect and describes, and a production method thereof, which is a method of optically resolving 1,1,3-trimethyl-4-aminoindane (racemate) represented by formula (2)

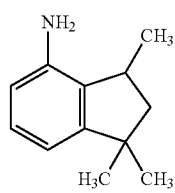
(2)

with D-tartaric acid in methanol. Patent Document 1, however, does not mention addition of water for the production of (R)-1,1,3-trimethyl-4-aminoindane.

PRIOR ART DOCUMENT

Patent Document

Patent Document 1: WO 2011/162397

SUMMARY OF THE INVENTION

Problems to be Solved by the Invention

Conventional methods for providing (R)-1,1,3-trimethyl-4-aminoindane with high optical purity require repeated recrystallization of a salt obtained by optical resolution, causing low yield of (R)-1,1,3-trimethyl-4-aminoindane. Thus, these methods are not industrially acceptable.

Means for Solving the Problems

The present inventions are as follows.

[1] A method for producing a methanol solvate of D-tartrate of (R)-1,1,3-trimethyl-4-aminoindane, the method comprising steps (a), (b), and (c) below, and comprising adding water to a reaction system before step (c):

step (a) of mixing 1,1,3-trimethyl-4-aminoindane, D-tartaric acid, and methanol to provide a mixture containing a methanol solvate of D-tartrate of (R)-1,1,3-trimethyl-4-aminoindane;

step (b) of cooling the obtained mixture; and step (c) of retrieving the methanol solvate of D-tartrate of (R)-1,1,3-trimethyl-4-aminoindane.

[2] The production method according to [1], wherein the amount of water used is from 0.01 to 0.15 parts by weight per part by weight of 1,1,3-trimethyl-4-aminoindane.

[3] The production method according to [1] or [2], wherein the cooling rate in step (b) is from 1° C. to 10° C./hour.

[4] The production method according to any one of [1] to [3], wherein the amount of D-tartaric acid used in step (a) is from 0.3 to 0.7 mol per mol of 1,1,3-trimethyl-4-aminoindane.

[5] The production method according to any one of [1] to [4], wherein the mixing temperature in step (a) is from 20° C. to 70° C.

[6] The production method according to any one of [1] to [5], wherein the amount of methanol used in step (a) is from 0.5 to 3 parts by weight per part by weight of 1,1,3-trimethyl-4-aminoindane.

[7] The production method according to any one of [1] to [6], wherein step (a) is a step of adding D-tartaric acid to a mixture of 1,1,3-trimethyl-4-aminoindane and methanol to provide the mixture containing the methanol solvate of D-tartrate of (R)-1,1,3-trimethyl-4-aminoindane.

[8] The production method according to any one of [1] to [7], wherein a solvent other than methanol is further mixed in step (a).

[9] The production method according to any one of [1] to [8], wherein the temperature after cooling in step (b) is from −20° C. to 30° C.

[10] The production method according to any one of [1] to [9], further comprising a step of distilling off methanol between steps (a) and (b).

[11] A method for producing (R)-1,1,3-trimethyl-4-aminoindane, the method comprising:

providing a methanol solvate of D-tartrate of (R)-1,1,3-trimethyl-4-aminoindane by the production method according to any one of [1] to [10]; and mixing the obtained methanol solvate of D-tartrate of (R)-1,1,3-trimethyl-4-aminoindane with an aqueous alkali metal hydroxide solution or aqueous alkali metal carbonate solution to provide (R)-1,1,3-trimethyl-4-aminoindane

[12] A method for producing a methanol solvate of D-tartrate of (R)-1,1,3-trimethyl-4-aminoindane, the method comprising steps (a'), (b'), and (c') below:

step (a') of mixing 1,1,3-trimethyl-4-aminoindane, D-tartaric acid, and methanol to provide a mixture containing a methanol solvate of D-tartrate of (R)-1,1,3-trimethyl-4-aminoindane;

step (b') of cooling the obtained mixture at a cooling rate of 1 to 10° C./hour; and step (c') of retrieving the methanol solvate of D-tartrate of (R)-1,1,3-trimethyl-4-aminoindane

[13] The production method according to [12], wherein the cooling rate in step (b') is from 1° C. to 8° C./hour.

[14] The production method according to [12], wherein the cooling rate in step (b') is from 3° C. to 6° C./hour.

[15] The production method according to any one of [12] to [14], wherein the amount of D-tartaric acid used in step (a') is from 0.3 to 0.7 mol per mol of 1,1,3-trimethyl-4-aminoindane.

[16] The production method according to any one of [12] to [15], wherein the mixing temperature in step (a') is from 20° C. to 70° C.

[17] The production method according to any one of [12] to [16], wherein the temperature after cooling in step (b') is from −20° C. to 30° C.

[18] The production method according to any one of [12] to [17], wherein the amount of methanol used in step (a') is from 0.5 to 3 parts by weight per part by weight of 1,1,3-trimethyl-4-aminoindane

[19] The production method according to any one of [12] to [18], wherein D-tartaric acid is added to the mixture of 1,1,3-trimethyl-4-aminoindane and methanol in step (a').

[20] The production method according to any one of [12] to [19], wherein a solvent other than methanol is further mixed in step (a').

[21] The production method according to any one of [12] to [20], further comprising a step of distilling off methanol between steps (a') and (b').

[22] A method for producing (R)-1,1,3-trimethyl-4-aminoindane, the method comprising:
providing a methanol solvate of D-tartrate of (R)-1,1,3-trimethyl-4-aminoindane by the production method according to any one of [12] to [21]; and
mixing the obtained methanol solvate of D-tartrate of (R)-1,1,3-trimethyl-4-aminoindane with an aqueous alkali metal hydroxide solution or aqueous alkali metal carbonate solution to provide (R)-1,1,3-trimethyl-4-aminoindane.

[23] A methanol solvate of D-tartrate of (R)-1,1,3-trimethyl-4-aminoindane.

Effect of the Invention

The production method of the present invention can produce (R)-1,1,3-trimethyl-4-aminoindane with high optical purity and high yield, which is industrially advantageous.

MODE FOR CARRYING OUT THE INVENTION

A first production method of the present invention is a method for producing a methanol solvate of D-tartrate of (R)-1,1,3-trimethyl-4-aminoindane, wherein the method comprises steps (a), (b), and (c) below, and comprises adding water to a reaction system before step (c):
step (a) of mixing 1,1,3-trimethyl-4-aminoindane, D-tartaric acid, and methanol to provide a mixture containing a methanol solvate of D-tartrate of (R)-1,1,3-trimethyl-4-aminoindane;
step (b) of cooling the obtained mixture; and
step (c) of retrieving the methanol solvate of D-tartrate of (R)-1,1,3-trimethyl-4-aminoindane.

A second production method of the present invention is a method for producing a methanol solvate of D-tartrate of (R)-1,1,3-trimethyl-4-aminoindane, wherein the method comprises steps (a'), (b'), and (c') below:
step (a') of mixing 1,1,3-trimethyl-4-aminoindane, D-tartaric acid, and methanol to provide a mixture containing a methanol solvate of D-tartrate of (R)-1,1,3-trimethyl-4-aminoindane;
step (b') of cooling the obtained mixture at a cooling rate of 1° C. to 10° C./hour; and
step (c') of retrieving the methanol solvate of D-tartrate of (R)-1,1,3-trimethyl-4-aminoindane.

First, step (a) will be described.
1,1,3-Trimethyl-4-aminoindane in step (a) is represented by formula (2) below. The optical purity of 1,1,3-trimethyl-4-aminoindane is not particularly limited, and usually includes 1,1,3-trimethyl-4-aminoindane with an optical purity of about 0% to 50% ee, preferably 1,1,3-trimethyl-4-aminoindane with an optical purity of 0% to 20% ee.

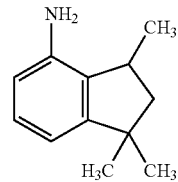

(2)

1,1,3-Trimethyl-4-aminoindane can be prepared, for example, by a method described in J. Chem. Soc. (C), 514 (1966).

Commercially available D-tartaric acid is usually used.
The amount of D-tartaric acid used is usually from 0.3 to 0.7 mol, preferably from 0.4 to 0.6 mol, more preferably from 0.45 to 0.55 mol per mol of 1,1,3-trimethyl-4-aminoindane.

The amount of methanol used is usually from 0.5 to 3 parts by weight, preferably from 0.6 to 2 parts by weight, more preferably from 0.8 to 2 parts by weight per part by weight of 1,1,3-trimethyl-4-aminoindane Water may be mixed at any time before step (c), and preferably mixed in step (a). Mixing water improves the filterability in step (c).

The amount of water used is usually from 0.01 to 0.15 parts by weight, preferably from 0.01 to 0.1 parts by weight per part by weight of 1,1,3-trimethyl-4-aminoindane.

Step (a) may be carried out in the presence of methanol, and optionally water and a solvent other than methanol and water. Examples of the solvent include alcohol solvents other than methanol such as ethanol and isopropanol; ether solvents such as tetrahydrofuran; nitrile solvents such as acetonitrile; ester solvents such as ethyl acetate; aromatic hydrocarbon solvents such as toluene, xylene, and ethylbenzene; halogenated aromatic hydrocarbon solvents such as monochlorobenzene; aliphatic hydrocarbon solvents such as heptane and hexane; and alicyclic hydrocarbon solvents such as cyclopentane and cyclohexane. These solvents may be combined, and the total amount of solvent(s) used other than methanol and water is usually 10 parts by weight or less per part by weight of 1,1,3-trimethyl-4-aminoindane.

Step (a) is preferably carried out by mixing 1,1,3-trimethyl-4-aminoindane, D-tartaric acid, methanol, and water. The mixing temperature is usually from 20° C. to 70° C., preferably from 30° C. to 50° C.

The mixing order is, for example, such that 1,1,3-trimethyl-4-aminoindane, D-tartaric acid, and methanol may be mixed at one time, or D-tartaric acid and methanol may be mixed first and then 1,1,3-trimethyl-4-aminoindane may be added to the obtained mixture. A mixture of D-tartaric acid and methanol may be added to 1,1,3-trimethyl-4-aminoindane. Alternatively, 1,1,3-trimethyl-4-aminoindane and methanol may be mixed and D-tartaric acid may be then added to the obtained mixture. Preferably, D-tartaric acid is added to a mixture of 1,1,3-trimethyl-4-aminoindane and methanol.

When water is mixed in step (a), the mixing order is, for example, such that 1,1,3-trimethyl-4-aminoindane, D-tartaric acid, methanol, and water may be mixed at one time, or D-tartaric acid, methanol, and water may be mixed first and then 1,1,3-trimethyl-4-aminoindane may be added to the obtained mixture. A mixture of D-tartaric acid, methanol, and water may be added to 1,1,3-trimethyl-4-aminoindane. Alternatively, D-tartaric acid, methanol, and 1,1,3-trimethyl-4-aminoindane may be mixed first and water may be then added to the obtained mixture. Alternatively, 1,1,3-trimethyl-4-aminoindane, methanol, and water may be mixed and D-tartaric acid may be then added to the obtained mixture. Preferably, D-tartaric acid is added to a mixture of 1,1,3-trimethyl-4-aminoindane, methanol, and water.

Addition may be performed at once or in aliquots. When D-tartaric acid is added to the mixture of 1,1,3-trimethyl-4-aminoindane and methanol, D-tartaric acid may be added at once, and preferably added in aliquots.

A mixture containing a methanol solvate of a D-tartrate of (R)-1,1,3-trimethyl-4-aminoindane is provided by mixing 1,1,3-trimethyl-4-aminoindane, D-tartaric acid, and methanol. Depending on the amount of methanol used and the mixing temperature, a portion of the produced methanol solvate of D-tartrate of (R)-1,1,3-trimethyl-4-aminoindane may deposit in the mixture.

(R)-1,1,3-Trimethyl-4-aminoindane is represented by formula (1) below.

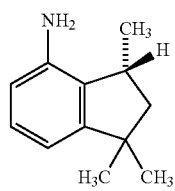

(1)

After step (a), a step of removing portions of methanol and optionally the solvent other than methanol from the mixture obtained in step (a) may be included. Removal is usually performed by concentrating the obtained mixture under vacuum. After portions of methanol and optionally the solvent other than methanol are removed, methanol, water, and a solvent other than methanol and water may be added to the residue of the mixture obtained in step (a).

Next, step (b) will be described. Step (b) is a step of cooling the mixture obtained in step (a).

The temperature after cooling is lower than the mixing temperature in step (a), preferably from −20° C. to 30° C., more preferably from −10° C. to 20° C.

The cooling rate is usually from 1° C. to 10° C./hour, and cooling the mixture obtained in step (a) at such a cooling rate deposits crystals of the methanol solvate of D-tartrate of (R)-1,1,3-trimethyl-4-aminoindane with high optical purity. The cooling rate is preferably from 1° C. to 8° C./hour, more preferably from 3° C. to 6° C./hour.

Water may be mixed in step (b). Water may be mixed while the mixture obtained in step (a) is cooled; or water may be mixed after cooling is once stopped and the mixture is cooled again; or water may be mixed after step (b). Mixing water improves the filterability in step (c).

After step (b), a step of removing portions of methanol and optionally the solvent other than methanol from the mixture obtained in step (b) may be included. The removal process is the same as the process of removing portions of methanol and optionally the solvent other than methanol after step (a).

Next, step (c) will be described. Step (c) is a step of retrieving the methanol solvate of D-tartrate of (R)-1,1,3-trimethyl-4-aminoindane from the mixture cooled in step (b).

The methanol solvate is usually retrieved by filtering the obtained mixture. Any filtering method can be used.

The retrieved methanol solvate is usually rinsed with at least one solvent selected from the group consisting of methanol, water, and the solvent other than methanol and water, and may be optionally dried.

By mixing the methanol solvate of D-tartrate of (R)-1,1,3-trimethyl-4-aminoindane with an aqueous alkali metal hydroxide solution or aqueous alkali metal carbonate solution, (R)-1,1,3-trimethyl-4-aminoindane can be provided.

Examples of the alkali metal hydroxide include sodium hydroxide and potassium hydroxide; and examples of the alkali metal carbonate include sodium carbonate.

The amount of the aqueous alkali metal hydroxide solution or aqueous alkali metal carbonate solution used is usually from 0.5 to 3 mol in terms of the alkali metal per mol of D-tartaric acid used in step (a).

The mixing temperature is usually from 10° C. to 80° C.

With regard to the concentration of the alkali metal hydroxide or alkali metal carbonate in the aqueous alkali metal hydroxide solution or aqueous alkali metal carbonate solution, the pH of the aqueous layer after mixing is preferably 9 or more, more preferably from 10 to 14.

Mixing may be performed in the presence of an organic solvent. Examples of the organic solvent include aromatic hydrocarbon solvents such as toluene, xylene, and ethylbenzene; halogenated aromatic hydrocarbon solvents such as monochlorobenzene; aliphatic hydrocarbon solvents such as heptane and hexane; alicyclic hydrocarbon solvents such as cyclopentane and cyclohexane; ether solvents such as diethyl ether and tert-butyl methyl ether; and ester solvents such as ethyl acetate. The amount of the organic solvent used is practically 10 parts by weight or less per part by weight of the methanol solvate.

The mixing order is, for example, such that the methanol solvate of D-tartrate of (R)-1,1,3-trimethyl-4-aminoindane, the aqueous alkali metal hydroxide or aqueous alkali metal carbonate solution, and optionally the organic solvent are mixed at one time; alternatively a mixture of the methanol solvate and optionally the organic solvent may be mixed with the aqueous alkali metal hydroxide or aqueous alkali metal carbonate solution. The methanol solvate may be added to a mixture of the aqueous alkali metal hydroxide solution or aqueous alkali metal carbonate solution and optionally the organic solvent. Preferably, the methanol solvate is added to a mixture of the organic solvent and the aqueous alkali metal hydroxide or aqueous alkali metal carbonate solution.

After the mixing is completed, (R)-1,1,3-trimethyl-4-aminoindane can be retrieved, for example, by separating the obtained mixture.

Next, step (a') will be described.

Step (a') is the same step as step (a).

Step (b') is the same step as step (b) except that a mixture obtained in step (a') is used instead of the mixture obtained in step (a) and the cooling rate is from 1 to 10° C./hour.

Step (c') is the same step as step (c) except that the mixture obtained in step (b') is used instead of the mixture obtained in step (b).

EXAMPLES

The present invention will be described below by way of Examples, but the present invention is not limited to these Examples.

Example 1

Under a nitrogen atmosphere at room temperature, 108.9 parts by weight of 1,1,3-trimethyl-4-aminoindane (purity:

91.9% by weight), 42.8 parts by weight (0.50 mol per mol of 1,1,3-trimethyl-4-aminoindane) of D-tartaric acid, and 108.6 parts by weight (1.09 parts by weight per part by weight of 1,1,3-trimethyl-4-aminoindane) of methanol were mixed. The obtained mixture was heated to 60° C. to provide a solution.

The obtained solution was cooled to 53° C. To the solution, a small amount of seed crystals of a methanol solvate of D-tartrate of (R)-1,1,3-trimethyl-4-aminoindane were added. After the solution was stirred at this temperature for three hours, the solution was cooled to 10° C. at a cooling rate of 5° C./hour and stirred at 10° C. for another 10 hours. The obtained mixture was filtered to retrieve crystals. The retrieved crystals were rinsed sequentially with 218.8 parts by weight of ice-cooled toluene and 217.3 parts by weight of heptane. The rinsed crystals were dried under vacuum to provide 79.9 parts by weight of a methanol solvate of D-tartrate of (R)-1,1,3-trimethyl-4-aminoindane. Analysis of the methanol solvate by high performance liquid chromatography (area percentage method) using a chiral column revealed that the ratio of R form/S form of 1,1,3-trimethyl-4-aminoindane was 97.6/2.4.

$^1$H-NMR data ($d_6$-dimethyl sulfoxide) of the methanol solvate of D-tartrate of (R)-1,1,3-trimethyl-4-aminoindane: δ (ppm) 6.85 (1H, t, J=7.6 Hz), 6.38 (1H, dd, J=7.6 Hz, 0.8 Hz), 6.36 (1H, dd, J=7.6 Hz, 0.8 Hz), 4.32 (2H, s), 3.24-3.06 (1H, m), 3.17 (3H, s), 2.09 (1H, dd, J=12.8 Hz, 8.8 Hz), 1.51 (1H, dd, J=12.8 Hz, 3.7 Hz), 1.22 (3H, s), 1.21 (3H, d, J=7.7 Hz), 1.14 (3H, s)

Example 2

Under a nitrogen atmosphere at room temperature, 108.8 parts by weight of 1,1,3-trimethyl-4-aminoindane (purity: 91.9% by weight) and 108.8 parts by weight (1.09 parts by weight per part by weight of 1,1,3-trimethyl-4-aminoindane) of methanol were mixed. After the obtained mixture was heated to 40° C., 43.2 parts by weight (0.50 mol per mol of 1,1,3-trimethyl-4-aminoindane) of D-tartaric acid was added in ten aliquots at 10-minute intervals.

After the obtained mixture was stirred at 40° C. for 24 hours, the mixture was cooled to 10° C. at a cooling rate of 5° C./hour and stirred at 10° C. for another 10 hours. The obtained mixture was filtered under vacuum to retrieve crystals. The retrieved crystals were rinsed sequentially twice with 217.6 parts by weight of ice-cooled toluene and once with 108.8 parts by weight of heptane. The rinsed crystals were dried under vacuum to provide 82.2 parts by weight of a methanol solvate of D-tartrate of (R)-1,1,3-trimethyl-4-aminoindane Analysis of the methanol solvate by high performance liquid chromatography (area percentage method) using a chiral column revealed that the ratio of R form/S form of 1,1,3-trimethyl-4-aminoindane was 97.5/2.5.

Example 3

Under a nitrogen atmosphere at room temperature, 54.4 parts by weight of 1,1,3-trimethyl-4-aminoindane (purity: 91.9% by weight), 54.4 parts by weight (1.09 parts by weight per part by weight of 1,1,3-trimethyl-4-aminoindane) of methanol, and 54.4 parts by weight of toluene were mixed. After the obtained mixture was heated to 40° C., 21.6 parts by weight (0.50 mol per mol of 1,1,3-trimethyl-4-aminoindane) of D-tartaric acid was divided into ten aliquots, and seven of the ten aliquots were added at 10-minute intervals. A small amount of seed crystals of a methanol solvate of D-tartrate of (R)-1,1,3-trimethyl-4-aminoindane were added and stirred for 10 minutes, and then the remaining three of the ten aliquots of D-tartaric acid were added at 10-minute intervals.

After the obtained mixture was stirred at 40° C. for one hour, the mixture was cooled to 10° C. at a cooling rate of 5° C./hour and stirred at 10° C. for another 10 hours. The obtained mixture was filtered under vacuum to retrieve crystals. At this time, the specific filtration resistance was 3.77× $10^{10}$ m/kg at 60 kPa, and the compressibility index was 0.64. The retrieved crystals were rinsed three times with 108.8 parts by weight of ice-cooled toluene. The rinsed crystals were dried under vacuum to provide 42.6 parts by weight of a methanol solvate of D-tartrate of (R)-1,1,3-trimethyl-4-aminoindane. Analysis of the methanol solvate by high performance liquid chromatography (area percentage method) using a chiral column revealed that the ratio of R form/S form of 1,1,3-trimethyl-4-aminoindane was 96.0/4.0.

Example 4

Under a nitrogen atmosphere at room temperature, 16.81 parts by weight of 1,1,3-trimethyl-4-aminoindane (purity: 95.1% by weight), 6.84 parts by weight (0.50 mol per mol of 1,1,3-trimethyl-4-aminoindane) of D-tartaric acid, and 16.81 parts by weight (1.05 parts by weight per part by weight of 1,1,3-trimethyl-4-aminoindane) of methanol were mixed. The obtained mixture was heated to 60° C. to provide a solution.

The obtained solution was cooled to 53° C. To the solution, a small amount of seed crystals of a methanol solvate of D-tartrate of (R)-1,1,3-trimethyl-4-aminoindane were added and stirred at this temperature for three hours. The solution was then cooled to 10° C. at a cooling rate of 5° C./hour and stirred at 10° C. for another 12 hours. The obtained mixture was filtered to retrieve crystals. The retrieved crystals were rinsed sequentially twice with 33.0 parts by weight of ice-cooled toluene and with 16.0 parts by weight of heptane. The rinsed crystals were mixed with 36.2 parts by weight of toluene to provide a slurry, and 28.1 parts by weight of a 15 wt % aqueous sodium hydroxide solution was added dropwise to the obtained slurry. The obtained mixture was stirred for one hour and then allowed to stand, followed by phase separation. The obtained organic layer was washed with 24.1 parts by weight of water and then concentrated under vacuum to provide 6.80 parts by weight of (R)-1,1,3-trimethyl-4-aminoindane. Analyzing the content of 1,1,3-trimethyl-4-aminoindane by a liquid chromatography internal standard method revealed that the content was 90.7% by weight and the retrieved ratio was 38.6%. Analysis of the optical purity by high performance liquid chromatography (area percentage method) using a chiral column revealed the ratio of R form/S form of 1,1,3-trimethyl-4-aminoindane was 97.6/2.4.

Example 5

Under a nitrogen atmosphere at room temperature, 105.3 parts by weight of 1,1,3-trimethyl-4-aminoindane (purity: 94.9% by weight), 63.0 parts by weight (0.63 parts by weight per part by weight of 1,1,3-trimethyl-4-aminoindane) of methanol, 4.0 parts by weight (0.04 parts by weight per part by weight of 1,1,3-trimethyl-4-aminoindane) of water, and 74.9 parts by weight of toluene were mixed. After the obtained mixture was heated to 40° C., 17.3 parts by weight (0.20 mol per mol of 1,1,3-trimethyl-4-aminoindane) of D-tartaric acid was added to provide a solution. To the obtained solution, a small amount of seed crystals of a methanol solvate of D-tartrate of (R)-1,1,3-trimethyl-4-aminoindane were added and stirred for one hour. Subsequently, 25.9 parts by weight (0.30 mol per mol of 1,1,3-trimethyl-4-aminoindane) of D-tartaric acid was added in six aliquots at 10-minute intervals.

After the obtained mixture was stirred at 40° C. for three hours, the mixture was cooled to 0° C. at a cooling rate of 5° C./hour and stirred at 0° C. for another 10 hours. The obtained mixture was filtered to retrieve crystals. The retrieved crystals were rinsed three times with 200.0 parts by weight of ice-cooled toluene. The rinsed crystals were dried under vacuum to provide 80.9 parts by weight of a methanol solvate of D-tartrate of (R)-1,1,3-trimethyl-4-aminoindane. Analysis of the methanol solvate by high performance liquid chromatography (area percentage method) using a chiral column revealed that the ratio of R form/S form of 1,1,3-trimethyl-4-aminoindane was 97.5/2.5.

Example 6

Under a nitrogen atmosphere at room temperature, 105.3 parts by weight of 1,1,3-trimethyl-4-aminoindane (purity: 94.9% by weight), 63.0 parts by weight (0.63 parts by weight per part by weight of 1,1,3-trimethyl-4-aminoindane) of methanol, 4.0 parts by weight (0.04 parts by weight per part by weight of 1,1,3-trimethyl-4-aminoindane) of water, and 74.9 parts by weight of toluene were mixed. After the obtained mixture was heated to 40° C., 12.9 parts by weight (0.15 mol per mol of 1,1,3-trimethyl-4-aminoindane) of D-tartaric acid was added to provide a solution. To the obtained solution, a small amount of seed crystals of a methanol solvate of D-tartrate of (R)-1,1,3-trimethyl-4-aminoindane were added and stirred for one hour. Subsequently, 30.2 parts by weight (0.35 mol per mol of 1,1,3-trimethyl-4-aminoindane) of D-tartaric acid was added in seven aliquots at 10-minute intervals.

After the obtained mixture was stirred at 40° C. for three hours, the mixture was cooled to 0° C. at a cooling rate of 5° C./hour and stirred at 0° C. for another four and half hours. The obtained mixture was filtered to retrieve crystals. At this time, the specific filtration resistance was $2.61 \times 10^9$ m/kg at 60 kPa, and the compressibility index was 0.26. The retrieved crystals were rinsed sequentially once with 70.0 parts by weight of a 1:9 (weight ratio) mixed solvent of ice-cooled methanol and toluene, and once with 100.0 parts by weight of ice-cooled toluene. The rinsed crystals were dried under vacuum to provide 84.2 parts by weight of a methanol solvate of D-tartrate of (R)-1,1,3-trimethyl-4-aminoindane. Analysis of the methanol solvate by high performance liquid chromatography (area percentage method) using a chiral column revealed that the ratio of R form/S form of 1,1,3-trimethyl-4-aminoindane was 97.1/2.9.

To a mixed solution containing 85.7 parts by weight of toluene, 81.5 parts by weight of a 28 wt % aqueous sodium hydroxide solution, and 81.5 parts by weight of water, 84.2 parts by weight of the methanol solvate of D-tartrate of (R)-1,1,3-trimethyl-4-aminoindane obtained above were added in six aliquots at 10-minute intervals. The obtained mixture was stirred for one hour and then allowed to stand, followed by phase separation. The obtained organic layer was washed with 85.7 parts by weight of water and then concentrated under vacuum to provide 60.1 parts by weight of (R)-1,1,3-trimethyl-4-aminoindane. Analyzing the content of 1,1,3-trimethyl-4-aminoindane by a liquid chromatography internal standard method revealed that the content was 67.9% by weight and the retrieved ratio from 1,1,3-trimethyl-4-aminoindane (racemate) was 40.8%. Analysis of the optical purity by high performance liquid chromatography (area percentage method) using a chiral column revealed the ratio of R form/S form of 1,1,3-trimethyl-4-aminoindane was 97.1/2.9.

Example 7

Under a nitrogen atmosphere at room temperature, 105.3 parts by weight of 1,1,3-trimethyl-4-aminoindane (purity: 94.9% by weight), 63.0 parts by weight (0.63 parts by weight per part by weight of 1,1,3-trimethyl-4-aminoindane) of methanol, 4.0 parts by weight (0.04 parts by weight per part by weight of 1,1,3-trimethyl-4-aminoindane) of water, and 74.9 parts by weight of toluene were mixed. After the obtained mixture was heated to 40° C., 12.9 parts by weight (0.15 mol per mol of 1,1,3-trimethyl-4-aminoindane) of D-tartaric acid was added to provide a solution. To the obtained solution, a small amount of seed crystals of a methanol solvate of D-tartrate of (R)-1,1,3-trimethyl-4-aminoindane were added and stirred for one hour. Subsequently, 30.2 parts by weight (0.35 mol per mol of 1,1,3-trimethyl-4-aminoindane) of D-tartaric acid was added in seven aliquots at 10-minute intervals.

After the obtained mixture was stirred at 40° C. for three hours, the mixture was cooled to 0° C. at a cooling rate of 5° C./hour and stirred at 0° C. for another nine hours. The obtained mixture was filtered to retrieve crystals. The retrieved crystals were rinsed once with 70.0 parts by weight of a 1:9 (weight ratio) mixed solvent of ice-cooled methanol and toluene. The rinsed crystals were dried under vacuum to provide 84.6 parts by weight of a methanol solvate of D-tartrate of (R)-1,1,3-trimethyl-4-aminoindane. Analysis of the methanol solvate by high performance liquid chromatography (area percentage method) using a chiral column revealed that the ratio of R form/S form of 1,1,3-trimethyl-4-aminoindane was 95.5/4.5.

Example 8

Under a nitrogen atmosphere at room temperature, 54.4 parts by weight of 1,1,3-trimethyl-4-aminoindane (purity: 91.9% by weight) and 43.5 parts by weight of toluene were mixed. The obtained mixture was heated to 40° C., and then a solution of 21.6 parts by weight (0.50 mol per mol of 1,1,3-trimethyl-4-aminoindane) of D-tartaric acid in a mixed solution of 4.4 parts by weight (0.09 parts by weight per part by weight of 1,1,3-trimethyl-4-aminoindane) of water and 39.2 parts by weight (0.78 parts by weight per part by weight of 1,1,3-trimethyl-4-aminoindane) of methanol was added dropwise to the above mixture over 4 hours while the mixture was incubated at 0° C.

After the obtained mixture was stirred at 40° C. for three hours, the mixture was cooled to 10° C. at a cooling rate of 5° C./hour and stirred at 10° C. for another three hours. The obtained mixture was filtered to retrieve crystals. The retrieved crystals were rinsed three times with 108.8 parts by weight of ice-cooled toluene. The rinsed crystals were dried under vacuum to provide 38.9 parts by weight of a methanol solvate of D-tartrate of (R)-1,1,3-trimethyl-4-aminoindane. Analysis of the methanol solvate by high performance liquid chromatography (area percentage method) using a chiral column revealed that the ratio of R form/S form of 1,1,3-trimethyl-4-aminoindane was 98.6/1.4.

Example 9

Under a nitrogen atmosphere at room temperature, 105.3 parts by weight of 1,1,3-trimethyl-4-aminoindane (purity: 94.9% by weight), and 200.0 parts by weight (2.0 parts by weight per part by weight of 1,1,3-trimethyl-4-aminoindane) of methanol were mixed. After the obtained mixture was heated to 40° C., 43.2 parts by weight (0.50 mol per mol of 1,1,3-trimethyl-4-aminoindane) of D-tartaric acid was added in 18 aliquots at 10-minute intervals. A small amount of seed crystals of a methanol solvate of D-tartrate of (R)-1,1,3-trimethyl-4-aminoindane were added and stirred for 15 minutes, and then the obtained mixture was concentrated under vacuum to distill off 109.1 parts by weight of methanol.

After the mixture was stirred at 40° C. for two hours, 9.1 parts by weight of methanol was added. Furthermore, 98.0 parts by weight of toluene was added dropwise over two hours, and then the mixture was cooled to 0° C. at a cooling rate of 5° C./hour and stirred at 0° C. for another three hours. The obtained mixture was filtered to retrieve crystals. The retrieved crystals were rinsed three times with 200.0 parts by weight of ice-cooled toluene. The rinsed crystals were dried under vacuum to provide 80.2 parts by weight of a methanol solvate of D-tartrate of (R)-1,1,3-trimethyl-4-aminoindane. Analysis of the methanol solvate by high performance liquid chromatography (area percentage method) using a chiral column revealed that the ratio of R form/S form of 1,1,3-trimethyl-4-aminoindane was 96.2/3.8.

INDUSTRIAL APPLICABILITY

The production method of the present invention can produce (R)-1,1,3-trimethyl-4-aminoindane with high optical purity and high yield, which is industrially advantageous.

The invention claimed is:

1. A method for producing a methanol solvate of a D-tartrate of (R)-1,1,3-trimethyl-4-aminoindane, the method comprising steps (a), (b), and (c) below, and comprising adding water to a reaction system before step (c):
    step (a) of mixing 1,1,3-trimethyl-4-aminoindane, D-tartaric acid, and methanol to provide a mixture containing a methanol solvate of D-tartrate of (R)-1,1,3-trimethyl-4-aminoindane;
    step (b) of cooling the obtained mixture; and
    step (c) of retrieving the methanol solvate of a D-tartrate of (R)-1,1,3-trimethyl-4-aminoindane.

2. The production method according to claim 1, wherein the amount of water used is from 0.01 to 0.15 parts by weight per part by weight of 1,1,3-trimethyl-4-aminoindane.

3. The production method according to claim 1, wherein the cooling rate in step (b) is from 1° C. to 10° C./hour.

4. The production method according to claim 1, wherein the amount of D-tartaric acid used in step (a) is from 0.3 to 0.7 mol per mol of 1,1,3-trimethyl-4-aminoindane.

5. The production method according to claim 1, wherein the mixing temperature in step (a) is from 20° C. to 70° C.

6. The production method according to claim 1, wherein the amount of methanol used in step (a) is from 0.5 to 3 parts by weight per part by weight of 1,1,3-trimethyl-4-aminoindane.

7. The production method according to claim 1, wherein step (a) is a step of adding D-tartaric acid to a mixture of 1,1,3-trimethyl-4-aminoindane and methanol to provide the mixture containing the methanol solvate of D-tartrate of (R)-1,1,3-trimethyl-4-aminoindane.

8. The production method according to claim 1, wherein a solvent other than methanol is further mixed in step (a).

9. The production method according to claim 1, wherein the temperature after cooling in step (b) is from −20° C. to 30° C.

10. The production method according to claim 1, further comprising a step of distilling off methanol between steps (a) and (b).

11. A method for producing (R)-1,1,3-trimethyl-4-aminoindane, the method comprising:
    providing a methanol solvate of D-tartrate of (R)-1,1,3-trimethyl-4-aminoindane by the production method according to claim 1; and
    mixing the obtained methanol solvate of D-tartrate of (R)-1,1,3-trimethyl-4-aminoindane with an aqueous alkali metal hydroxide solution or aqueous alkali metal carbonate solution to provide (R)-1,1,3-trimethyl-4-aminoindane.

12. A method for producing a methanol solvate of D-tartrate of (R)-1,1,3-trimethyl-4-aminoindane, the method comprising steps (a'), (b'), and (c') below:
    step (a') of mixing 1,1,3-trimethyl-4-aminoindane, D-tartaric acid, and methanol to provide a mixture containing a methanol solvate of D-tartrate of (R)-1,1,3-trimethyl-4-aminoindane;
    step (b') of cooling the obtained mixture at a cooling rate of 1 to 10° C./hour; and
    step (c') of retrieving the methanol solvate of D-tartrate of (R)-1,1,3-trimethyl-4-aminoindane; and
    wherein a solvent other than methanol is further mixed in step (a').

13. A method for producing a methanol solvate of D-tartrate of (R)-1,1,3-trimethyl-4-aminoindane, the method comprising steps (a'), (b'), and (c') below:
    step (a') of mixing 1,1,3-trimethyl-4-aminoindane, D-tartaric acid, and methanol to provide a mixture containing a methanol solvate of D-tartrate of (R)-1,1,3-trimethyl-4-aminoindane;
    step (b') of cooling the obtained mixture at a cooling rate of 1 to 10° C./hour; and
    step (c') of retrieving the methanol solvate of D-tartrate of (R)-1,1,3-trimethyl-4-aminoindane; and
    further comprising a step of distilling off methanol between steps (a') and (b').

* * * * *